United States Patent [19]

Kraatz et al.

[11] Patent Number: 4,804,766

[45] Date of Patent: * Feb. 14, 1989

[54] PROCESS FOR THE PREPARATION OF THE (−)-ANTIPODE OF (E)-1-CYCLOHEXYL-4,4-DIMETHYL-3-HYDROXY-2-(1,2,4-TRIAZOL-1-YL)-PENT-1-ENE

[75] Inventors: Udo Kraatz, Leverkusen; Peter Feyen, Mettmann, both of Fed. Rep. of Germany

[73] Assignee: Bayer Aktiengesellschaft, Leverkusen, Fed. Rep. of Germany

[*] Notice: The portion of the term of this patent subsequent to Dec. 6, 2005 has been disclaimed.

[21] Appl. No.: 835,587

[22] Filed: Mar. 3, 1986

[30] Foreign Application Priority Data

Mar. 19, 1985 [DE] Fed. Rep. of Germany ....... 3509823

[51] Int. Cl.⁴ .......................................... C07D 249/08
[52] U.S. Cl. .................................................... 548/262
[58] Field of Search ........................................ 548/262

[56] References Cited

U.S. PATENT DOCUMENTS

| | | | |
|---|---|---|---|
| 4,592,772 | 6/1986 | Kraatz et al. | 548/262 |
| 4,607,108 | 8/1986 | Feyen et al. | 548/262 |

FOREIGN PATENT DOCUMENTS

| | | | |
|---|---|---|---|
| 0054431 | 6/1982 | European Pat. Off. | 548/262 |
| 0142566 | 5/1985 | European Pat. Off. | 548/262 |
| 3102588 | 8/1982 | Fed. Rep. of Germany | |
| 3208142 | 9/1983 | Fed. Rep. of Germany | |
| 3221700 | 12/1983 | Fed. Rep. of Germany | |
| 3235050 | 3/1984 | Fed. Rep. of Germany | 548/262 |
| 3302120 | 7/1984 | Fed. Rep. of Germany | |
| 03885 | 11/1984 | PCT Int'l Appl. | |

OTHER PUBLICATIONS

Tanno et al., "Asymmetrical Reduction of Various, etc" Chem Pharm Bull (1983) 837.

Chem. Pharm. Bull., 837 (1983), No. 3, vol. 31 pp. 837-851.
Chemical Abstracts, vol. 94, No. 17, Apr. 27, 1981, Abstract 139814c, p. 767.

*Primary Examiner*—Glennon H. Hollrah
*Assistant Examiner*—Patricia L. Morris
*Attorney, Agent, or Firm*—Sprung Horn Kramer & Woods

[57] ABSTRACT

A process for the preparation of the (−)-antipode of (E)-1-cyclohexyl-4,4-dimethyl-3-hydroxy-2-(1,2,4-triazol-1-yl)-pent-1-ene of the formula

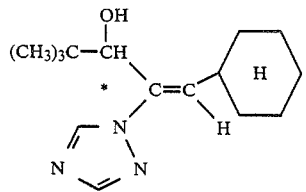

which comprises reacting the (E)-isomer of 1-cyclohexyl-4,4-dimethyl-2-(1,2,4-triazol-1-yl)-pent-1-en-3-one of the formula

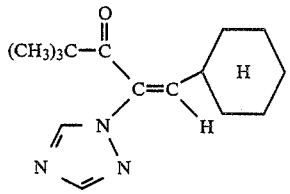

with lithium aluminum hydride in the presence of an inert organic diluent and in the presence of a chiral aminoalcohol at a temperature between −70° C. and +50° C. The (−)-antipode is produced in high selectivity, using (−)-N-methyl-ephedrine.

4 Claims, No Drawings

PROCESS FOR THE PREPARATION OF THE (−)-ANTIPODE OF (E)-1-CYCLOHEXYL-4,4-DIMETHYL-3-HYDROXY-2-(1,2,4-TRIAZOL-1-YL)-PENT-1-ENE

The present invention relates to a new process for the preparation of the known (−)-antipode of (E)-1-cyclohexyl-4,4-dimethyl-3-hydroxy-2-(1,2,4-triazol-1-yl)pent-1-ene.

As employed herein the (−)-antipode is that enantiomer which rotates the plane of vibration of linearly polarized light of the sodium D line to the left.

It has already been disclosed that the (−)-antipode of (E)-1-cyclohexyl-4,4-dimethyl-3-hydroxy-2-(1,2,4-triazol-1-yl)-pent-1-ene can be prepared by reacting the corresponding racemic compound with an optically active acid chloride, separating the resulting ester diastereomer mixture by a chromatographic method, and hydrolyzing the ester which contains the (−)-antipode (see DE-OS (German Published Specification) 3,302,122). However, the disadvantage of this process is that it is only suitable for the synthesis of small amounts of the desired antipode.

It has also been disclosed that ketones can be reduced to optically active carbinols with reducing agents in the presence of various chiral auxiliary reagents (see Chem. Pharm. Bull. 31, 837 (1983) and EP-OS (European Published Specification) 0,054,431). However, the fact that this process is not generally applicable is unsatisfactory. Thus, ketones which do not contain any aromatic groups can only be converted to carbinols with an optical purity insufficient for practical purposes.

It has now been found that the (−)-antipode of (E)-1-cyclohexyl-4,4-dimethyl-3-hydroxy-2-(1,2,4-triazol-1-yl)-pent-1-ene of the formula

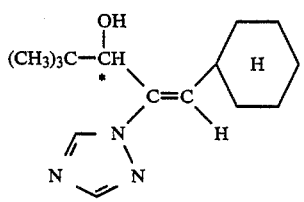

(I)

is obtained by a process in which the (E)-isomer of 1-cyclohexyl-4,4-dimethyl-2-(1,2,4-triazol-1-yl)-pent-1-en-3-one of the formula

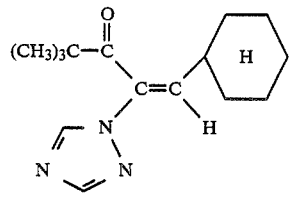

(II)

is reacted with lithium aluminum hydride in the presence of an inert organic diluent and in the presence of a chiral aminoalcohol and, if appropriate, in the presence of an amine, at temperatures between −70° C. and +50° C.

It must be regarded as extremely surprising that the (−)-antipode of (E)-1-cyclohexyl-4,4-dimethyl-3-hydroxy-2-(1,2,4-triazol-1-yl)-pent-1-ene of the formula (I) can be prepared in very high yield and excellent purity by the process according to the invention, since, on the basis of the known prior art, it was not to be expected that the reaction would lead selectively to the desired product. In particular, it was not to be expected that the reaction would take place virtually without any side reactions even at relatively high temperatures.

The process according to the invention is distinguished by a number of advantages. Thus, the reactants are also obtainable in fairly large amounts and can furthermore be handled on an industrial scale without difficulty. Moreover, the outlay in terms of apparatus required for carrying out the process is small, and no difficulties are encountered in working up the reaction mixture obtained when the reaction is complete. In particular, however, the (−)-antipode of (E)-1-cyclohexyl-4,4-dimethyl-3-hydroxy-2-(1,2,4-triazol-1-yl)-pent-1-ene of the formula (I) can be prepared by the process according to the invention in higher yield and better optical purity than by the method known to date, in which a classical resolution of a racemate is carried out.

Formula (I) gives an unambiguous definition of the (−)-antipode of (E)-1-cyclohexyl-4,4-dimethyl-3-hydroxy-2-(1,2,4-triazol-1-yl)-pent-1-ene which can be prepared by the process according to the invention. In this formula, the asymmetrically substituted carbon atom, which constitutes the chiral centre, is denoted by an (*). The letter "E" in front of the systematic name of the compound of the formula (I) indicates that the cyclohexyl radical and the 1,2,4-triazolyl radical are located on opposite sides of the double bond.

If lithium aluminum hydride is used as the reducing agent, the (−)-antipode of N-methylephedrine as the chiral auxiliary reagent and N-ethyl-aniline as the additional amine, the course of the process according to the invention can be represented by the following equation:

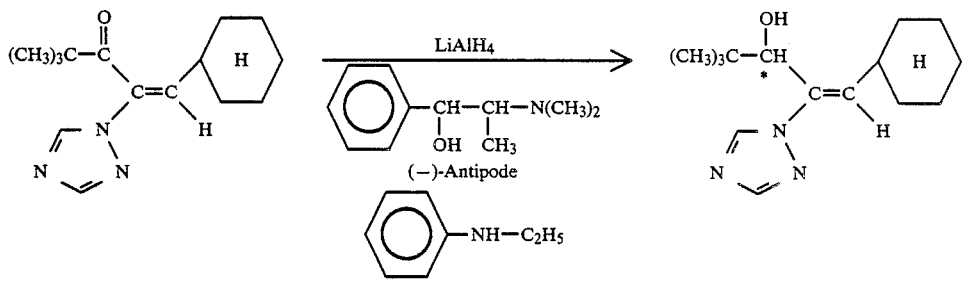

The E-isomer of 1-cyclohexyl-4,4-dimethyl-2-(1,2,4-triazol-1-yl)-pent-1-en-3-one of the formula (II) which is required as a starting material for carrying out the process according to the invention is already known (see U.S. Pat. No. 4,607,108.

In carrying out the process according to the invention, lithium aluminum hydride acts as reducing agent.

Diluents which can be used in the reaction according to the invention are all inert organic solvents which are customarily employed for reactions of this type. Ethers, such as diethyl ether, tetrahydrofuran and tert.-butyl methyl ether, are preferred.

Suitable chiral auxiliary reagents for carrying out the process according to the invention are optically active aminoalcohols. The (—)-antipode of N-methyl-ephedrine is particularly preferred.

Amines which can, if required, be employed for carrying out the process according to the invention are preferably secondary amines. N-ethyl-aniline is particularly preferred.

In carrying out the process according to the invention, the reaction temperatures can be varied within a certain range. In general, the reaction is carried out at temperatures between −70° C. and +50° C., preferably between −20° C. and +40° C.

The process according to the invention is carried out in general under atmospheric pressure.

The reaction is preferably carried out under a protective gas atmosphere. All customary gases which are inert under the reaction conditions can be employed as protective gases. Nitrogen and argon are preferably used.

In carrying out the process according to the invention, 1 to 3 mols, preferably 1.3 to 2 mols, of lithium aluminum hydride and 1 to 3 mols, preferably 1.3 to 2 mols, of a chiral aminoalcohol and, if appropriate, 2 to 4 mols, preferably 2.5 to 3.5 mols, of an additional amine are generally employed per mol of (E)-isomer of 1-cyclohexyl-4,4-dimethyl-2-(1,2,4-triazol-1-yl)-pent-1-en-3-one of the formula (II).

In carrying out the process according to the invention, the following procedure is generally followed: the chiral aminoalcohol, if appropriate dissolved in an organic diluent, is added dropwise to a suspension of lithium aluminum hydride in an organic diluent at temperatures between 0° C. and 50° C., preferably between 10° C. and 40° C., the amine is then added if required, and a solution of the (E)-isomer of 1-cyclohexyl-4,4-dimethyl-2-(1,2,4-triazol-1-yl)-pent-1-en-3-one of the formula (II) in an organic diluent is then added dropwise at temperatures between −70° C. and 0° C., preferably between −20° C. and −10° C. Working up is carried out by customary methods. In general, the procedure is as follows: water is added, the reaction mixture is acidified, the organic phase is separated off, the aqueous phase is extracted several times with an organic solvent which is poorly miscible with water, and the combined organic phases are washed with water and then evaporated down. The residue which remains can be further purified by digestion with suitable organic solvents or by recrystallization.

The (—)-antipode of (E)-1-cyclohexyl-4,4-dimethyl-3-hydroxy-2-(1,2,4-triazol-1-yl)-pent-1-ene of the formula (I) which can be prepared by the process according to the invention, and its use for regulating plant growth, are known (see DE-OS (German Published Specification) 3,302,122).

The method for carrying out the process according to the invention is illustrated by the example which follows.

Preparation example

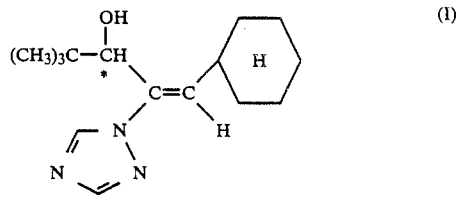

(I)

A solution of 628 g (3.5 mols) of the (—)-antipode of N-methyl-ephedrine in 7.5 liters of tert.-butyl methyl ether is added dropwise to a suspension of 133 g (3.5 mols) of lithium aluminum hydride in 1.5 liters of tert.-butyl methyl ether in the course of 45 minutes at 20° C. under an argon atmosphere. Stirring is continued for 30 minutes at 40° C., after which the mixture is cooled to 10° C., and 848 g (7 mols) of N-ethyl-aniline are added in the course of 45 minutes. The mixture is stirred for a further hour at 40° C. and then cooled to −15° C., and a solution of 522 g (2 mols) of the (E)-isomer of 1-cyclohexyl-4,4-dimethyl-2-(1,2,4-triazol-1-yl)-pent-1-en-3-one in 4.7 liters of tert.-butyl methyl ether is then added dropwise in the course of 30 minutes, the temperature of the reaction mixture being kept at −10° C. to −15° C. The mixture is stirred for a further 16 hours at −15° C., and 8 liters of water are then added slowly. 3.5 liters of 10% strength aqueous hydrochloric acid are added to the resulting reaction mixture. Thereafter, the organic phase is separated off, and the aqueous phase is extracted with three times 2.5 liters of tert.-butyl methyl ether. The combined organic phases are washed with twice 2 liters of water and then evaporated down under a pressure of 20 mbar. The crystalline residue which remains is stirred with cyclohexane, and the product is filtered off under suction and dried under reduced pressure at 35° C. In this manner, 466 g (87% of theory) of the (—)-antipode of (E)-1-cyclohexyl-4,4-dimethyl-3- hydroxy-2-(1,2,4-triazol-1-yl)-pent-1-ene are obtained in the form of a crystalline product.

Melting point: 162°-164° C.

$[\alpha]_D^{20} = -81.4°$ (C=67 mg/10ml of CHCl$_3$)

The product has an optical purity of 100%.

It is understood that the specification and examples are illustrative but not limitative of the present invention and that other embodiments within the spirit and scope of the invention will suggest themselves to those skilled in the art.

We claim:

1. A process for the preparation of the (−)-antipode of (E)-1-cyclohexyl-4,4-dimethyl-3-hydroxy-2-(1,2,4-triazol-1-yl)-pent-1-ene of the formula

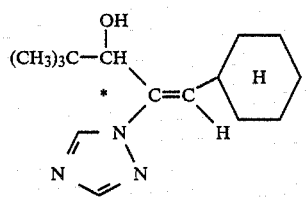

which comprises reacting the (E)-isomer of 1-cyclohexyl-4,4-dimethyl-2-(1,2,4-triazol-1-yl)-pent-1-en-3-one of the formula

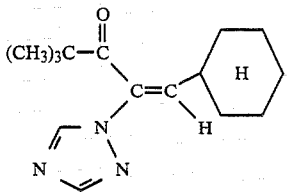

with lithium aluminum hydride in the presence of an inert organic diluent in the presence of the (−)-antipode of N-methyl-ephedrine and in the presence of N-ethylaniline at a temperature between −20° C. and 0° C.

2. A process according to claim 1, wherein the inert organic diluent is diethyl ether, tetrahydrofuran or tert.-butyl methyl ether.

3. A process according to claim 1, wherein 1 to 3 mols of lithium aluminum hydride and 1 to 3 mols of the chiral aminoalcohol are employed per mol of the (E)-isomer of 1-cyclohexyl-4,4-dimethyl-2-(1,2,4-triazol-1-yl)-pent-1-en-3-one.

4. A process according to claim 3, wherein during the reaction there are also present 2 to 4 mols of an amine.

* * * * *